United States Patent [19]

Lunn

[11] Patent Number: 5,509,910
[45] Date of Patent: Apr. 23, 1996

[54] METHOD OF SOFT TIP ATTACHMENT FOR THIN WALLED CATHETERS

[75] Inventor: Peter A. Lunn, Beverly, Mass.

[73] Assignee: Medtronic, Inc., Minneapolis, Minn.

[21] Appl. No.: 236,765

[22] Filed: May 2, 1994

[51] Int. Cl.⁶ ................................... A61M 25/00
[52] U.S. Cl. ................. 604/282; 604/264; 604/280
[58] Field of Search ............................. 604/264, 280, 604/282; 128/658

[56] References Cited

U.S. PATENT DOCUMENTS

| | | | |
|---|---|---|---|
| 4,283,447 | 8/1981 | Flynn | 128/658 |
| 4,531,943 | 7/1985 | Van Tassel et al. | |
| 4,540,404 | 9/1985 | Wolvek | 604/96 |
| 4,551,292 | 11/1985 | Fletcher et al. | |
| 4,563,181 | 1/1986 | Wijayarathna et al. | |
| 4,863,442 | 9/1989 | DeMello et al. | |
| 4,886,506 | 12/1989 | Lovgren et al. | |
| 4,899,787 | 2/1990 | Ouchi et al. | |
| 4,921,483 | 5/1990 | Wijay et al. | 606/194 |
| 4,931,037 | 6/1990 | Wetterman | 604/280 |
| 5,078,702 | 1/1992 | Pomeranz | |
| 5,160,559 | 11/1992 | Scovil et al. | |
| 5,178,158 | 1/1993 | de Toledo | 604/282 |
| 5,205,830 | 4/1993 | Dassa et al. | 604/280 |
| 5,221,270 | 6/1993 | Parker | 604/282 |
| 5,234,416 | 8/1993 | Macaulay et al. | |
| 5,279,596 | 1/1994 | Castaneda et al. | 604/280 |
| 5,292,311 | 3/1994 | Cope | 604/264 |
| 5,342,383 | 8/1994 | Thomas | 606/191 |

FOREIGN PATENT DOCUMENTS 8909634  10/1989  WIPO ...................... 604/282

*Primary Examiner*—Corrine M. Maglione
*Assistant Examiner*—N. Kent Gring
*Attorney, Agent, or Firm*—Dianne M. F. Plunkett; Harold R. Patton

[57] ABSTRACT

A catheter comprising a soft tip segment (5), a transition segment (11), and a shaft segment (3). The soft tip segment (5) has at least two ungular sections (6, 7) removed from the proximal end. The distal end of the transition segment (11) is bonded to the proximal end of the soft tip (5) segment. The transition segment (11) is comprised of materials having substantially higher tensile strength than the soft tip (5) segment. The distal end of the shaft (3) is bonded to the proximal end of the transition segment (11). The distal end of the shaft (3) has at least two ungular sections (2, 4) removed.

18 Claims, 4 Drawing Sheets

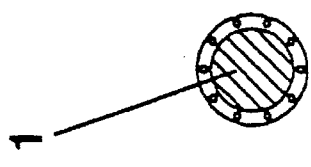
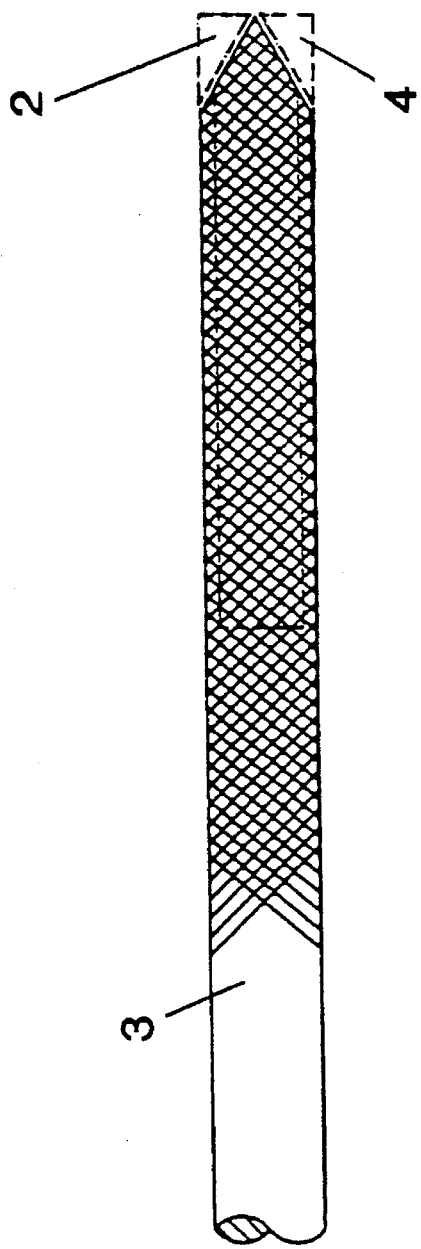

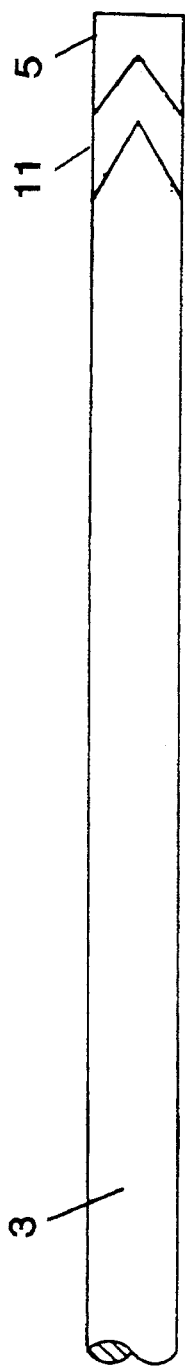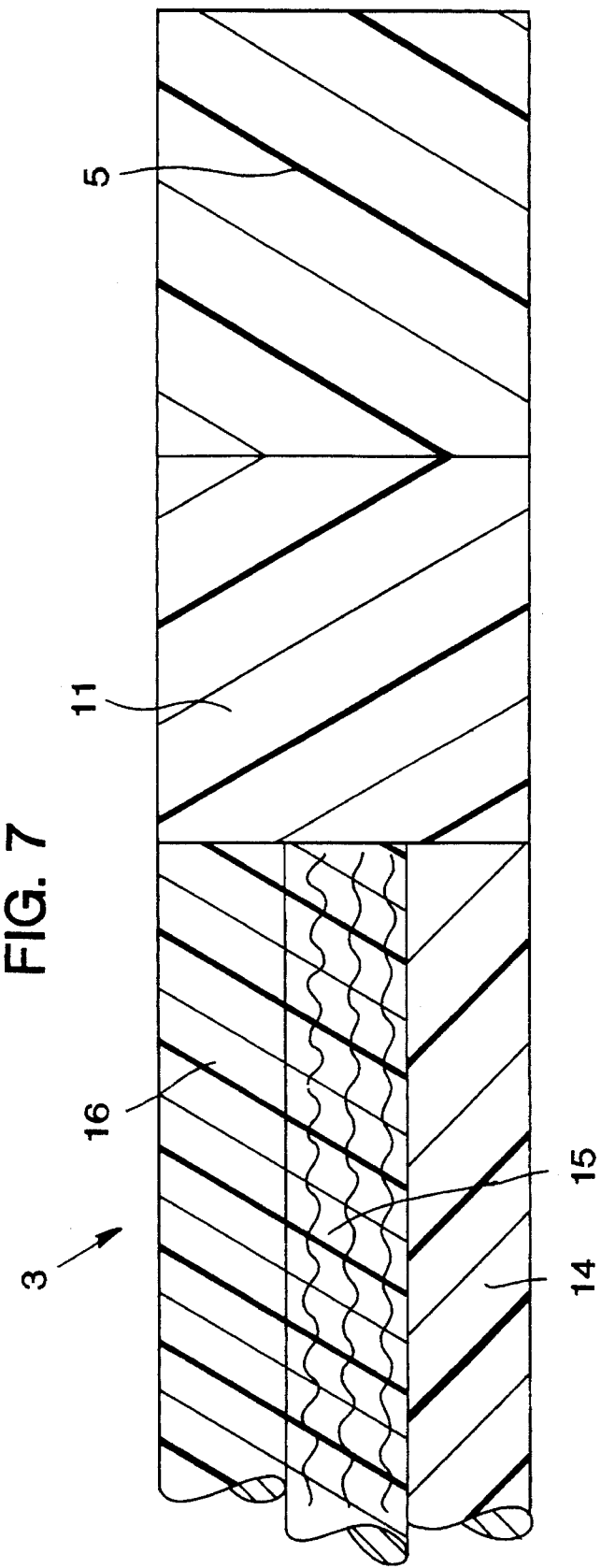
FIG. 6
FIG. 7

METHOD OF SOFT TIP ATTACHMENT FOR THIN WALLED CATHETERS

FIELD OF THE INVENTION

Catheters are tube-like members which are inserted into the body for diagnostic or therapeutic reasons. One of the therapeutic procedures applicable to the present invention is known as percutaneous transluminal coronary angioplasty ("PTCA"). PTCA can be used, for example, to reduce arterial build-up of cholesterol fats or atherosclerotic plaque. Catheters must have sufficient stiffness to be pushed through vessels as well as rigidity to provide a high degree of torsional control. Stiffness or rigidity in the catheter tip poses the danger of puncturing or otherwise damaging a vessel as it twists through the vascular system. It is therefore desirable for catheters to have a soft or flexible distal tip. The trend toward catheters with wall thicknesses of less than 0.3 mm and a softer distal tip results, however, in a substantially weaker bond between the soft distal tip and the catheter shaft. The present invention solves this problem.

BACKGROUND OF THE INVENTION

U.S. Pat. No. 4,531,943 issued to Van Tassel et al., discloses a soft deformable tip member attached to the distal end of a catheter shaft where the tip member includes a circumferential fold line to increase the area of contact between the tip member and body tissue when a force is exerted on the catheter shaft. To attach the tip member to the distal end of the catheter shaft. The exterior surface of the distal end of the catheter shaft is ground circumferentially using a centerless grinder to reduce the distal shaft wall thickness. The tip member is then fitted over the distal end of the catheter shaft to form a lap joint with the distal shaft and is then bonded to the distal shaft using an adhesive or other bonding technique. This lap joint design is undesirable because it creates a stress concentration area at the distal end of the catheter shaft in a plane perpendicular to the longitudinal axis of the catheter shaft. The effect of this stress concentration is an unacceptably low bond strength between the catheter shaft and the soft tip member when the wall thickness of the catheter shaft is less than 0.3 mm.

U.S. Pat. No. 4,551,292, issued to Fletcher et al., discloses a method of forming a soft deformable tip member at the distal end of a catheter shaft where the distal end of the catheter shaft is initially prepared for soft tip attachment by circumferentially centerless grinding the shaft to form a taper or frusto-conical shape of a predetermined angle. The grinding operation reduces the wall thickness of the distal end of the catheter shaft and the tip member is subsequently fitted over the distal shaft. The tip member and catheter shaft are then bonded together using a technique such as injection molding. While this lap joint design increases the surface area of contact between the tip member and the catheter shaft over that of the '943 Van Tassel patent, supra, thereby increasing the potential bond strength of the joint, the joint does not yield adequate bond strength when the wall thickness of the catheter shaft is less than 0.3 mm and the tip member is of a soft, typically low tensile strength material such as 70A Shore durometer PEBAX® polyether-polyamide.

U.S. Pat. No. 4,563,181, issued to Wijayarathna et al., discloses a soft tip member which is bonded to the distal end of the catheter shaft by employing a butt-joint between the tip and shaft. Heat and pressure are used to join the tip member to the catheter shaft, the materials for which are chosen by similarity of their chemical properties so that a bond is achieved. This butt joint design does not yield adequate bond strength because of the low surface area of contact between the tip member and the distal catheter shaft and the stress concentration area at the distal end of the catheter shaft in a plane perpendicular to the longitudinal axis of the catheter shaft. The low bond strength of such a design is particularly evident where the catheter shaft wall thickness is less than 0.3 mm and the tip member is of a soft, typically low tensile strength material such as a blend of nylon-11 and polyether block amide.

U.S. Pat. No. 4,863,442, issued to DeMello et al., discloses a soft tip member which is bonded to the distal end of the catheter shaft by employing an overlap of the tip member to the core layer of the distal end of the catheter shaft. The distal end of the catheter shaft is skived circumferentially approximately two millimeters proximal to the distal end and the outer layer of the catheter shaft is removed to reduce the outer diameter of the distal end. The soft tip member is then forced over the reduced diameter distal end and bonded to the catheter shaft using techniques such as injection molding or heat in combination with a tubular shrink film. This overlapping joint design, similar to the '943 Van Tassel patent, supra, is undesirable because it creates a stress concentration area at the distal end of the catheter shaft in a plane perpendicular to the longitudinal axis of the catheter shaft yielding inadequate bond strength when the catheter shaft wall thickness is less than 0.3 mm.

U.S. Pat. No. 4,886,506 issued to Lovgren et al., discloses a soft tip member which is bonded to the distal end of the catheter shaft by employing a tapered portion of the distal shaft which defines a frusto-conically-shaped outer surface. The tip member is fitted coaxially over the tapered portion of the distal shaft and then bonded to the shaft using RF welding. This joint design, similar to the '292 Fletcher patent, supra, does not yield adequate bond strength when the wall thickness of the catheter shaft is less than 0.3 mm and the tip member is of a soft, typically low tensile strength material such as 25D Shore durometer PEBAX®.

U.S. Pat. No. 4,899,787, issued to Ouchi et al., discloses a flexible tube having two or more tube sections which are bonded to a tubular core which comprises one or more fabric mesh tubes and one or more metallic tubular spirals. The tube sections are butted together and then fused to the tubular core. A catheter utilizing this tubular core structure possesses undesirable stiffness and rigidity because of the presence of mesh tubes and metallic tubular spirals at the distal end of the catheter shaft. As a result, the tubular core poses the danger of puncturing or otherwise damaging a vessel as the catheter is manipulated through the vascular system.

U.S. Pat. No. 5,078,702 issued to Pomeranz discloses a soft tip member which is bonded to the distal end of the catheter shaft by employing a sloping surface of the distal shaft over which the tip member is placed for fusing. The lap joint between the tip member and the distal shaft is attained by circumferentially grinding or machining the distal end of the catheter shaft to remove the outer polymer sheath and expose the inner polymer sheath. The tip is expanded and then placed over the ground end of the shaft or the subsequent fusing operation. The sloping surface lap joint design, similar to the '292 Fletcher and the '506 Lovgren patents, supra, yields inadequate bond strength when the catheter shaft wall thickness is less than 0.3 mm and the tip member is of a soft, typically low tensile strength material such as 70A or 25D Shore durometer PEBAX®.

U.S. Pat. No. 5,160,559, issued to Scovil et al., discloses a soft tip member which is bonded to the distal end of the catheter shaft by mating a proximal end of the soft tip member to the distal end of the catheter shaft to form a butt joint. The butt joint is then softened with a heat and pressure source to render the mating end flowable. A lap joint is formed between the flowable mating ends when the proximal end of the tip member forms a tapered apex that extends proximally and the distal end of the catheter shaft forms a V-shaped groove that widens distally. This tapered apex joint design does not yield adequate bond strength, however, when the wall thickness of the catheter shaft is less than 0.3 mm and the tip member is of a soft, typically low tensile strength material.

U.S. Pat. No. 5,234,416, issued to Macaulay et al., discloses a distal soft tip comprising at least two relatively short, coaxially disposed flexible tubular elements. The "first tubular element" 17 is secured to the "distal section" 13 of the catheter shaft, and the "second tubular element" 18 which is softer than the "first tubular element" 17 is secured to the "first tubular element" 17. The "first tubular element" 17 incorporates a radiopaque filler to make the distal tip fluoroscopically observable. See col. 5, lns 32–35. The "first tubular element" 17 has a durometer in the range of Shore 80A to 100A while the "second tubular element" 18 has a durometer in the Shore 70A to 90A range. See col. 6, lns 54–59. The distal end of the catheter shaft has a circumferential shoulder over which the proximal end of the first tubular element, which is stepped to mate with the shoulder, is placed. The proximal end of the "second tubular element" 18 is abutted against the distal end of the "first tubular element" 17. The short tubular elements are joined with the distal end of the catheter shaft by means such as melt fusing or adhesive bonding.

The joints employed to bond the tubular elements of the '416 Macaulay patent suffer from the same problems as the above-referenced prior art. The overlapping joint of the "first tubular element" 17 with the "distal section" 13 of the catheter shaft, similar to the '943 Van Tassel patent, supra, is undesirable because it creates a stress concentration area at the distal end of the catheter shaft in a plane perpendicular to the longitudinal axis of the catheter shaft. The effect of this stress concentration is an unacceptably low bond strength between the catheter shaft and the "first tubular element" 17 when the wall thickness of the catheter shaft is less than 0.3 mm. Further, the butt joint design of the "second tubular element" 18 with the "first tubular element" 17, similar to the '181 Wijayarathna patent, supra, does not yield adequate bond strength because of the low surface area of contact and the stress concentration area at the junction of the "first and second tubular elements" 17 and 18 in a plane perpendicular to the longitudinal axis of the catheter shaft. The effect of the low surface area and the stress concentration is inadequate bond strength when the catheter shaft wall thickness is less than 0.3 mm and when soft, typically low tensile strength materials, such as Shore 70A to 90A Tecoflex® are used for the "second tubular element" 18.

In the commonly-owned copending application of Brin et al. with a common inventor, U.S. application Ser. No. 08/083,840, for which a continuation-in-part is being filed, an improved method of soft tip attachment is disclosed where a lap joint is produced through heat and pressure between the distal end of the catheter shaft, a high tensile strength transition segment, and a distal soft tip. The presence of wire braid and TEFLON® (polytetrafluoroethylene or PTFE) in a typical multi-layer catheter shaft compromises the bond between the catheter shaft and a distal tip segment since the materials used for the soft tip do not bond well to wire braid or to TEFLON®. Thus, a transition segment is utilized between the distal end of the catheter shaft and the distal tip segment which is comprised of materials with a high tensile strength relative to the materials comprising the soft tip. As a result, the high strength of the transition segment compensates for the compromised bonding with the multi-layer catheter shaft and yields acceptable bond strength with the distal soft tip. The use of a high tensile strength transition segment is particularly important to achieving acceptable bond strength where the catheter wall thickness is less than 0.3 mm and when the soft tip material is a low tensile strength material, such as Shore 80A Pellethane® polyurethane. A problem which arises with the above invention, however, is that the lap joint which bonds the catheter shaft, transition segment, and distal soft tip is attained through substantial heat and pressure which can have the adverse effects on the concentricity, stiffness, and kink resistance of the catheter shaft. Thus, an improved soft tip is needed which provides adequate bond strength to the catheter shaft where the wall thickness of the catheter shaft is less than 0.3 mm and the tip material is of the requisite softness without compromising concentricity, stiffness, or kink resistance of the catheter shaft. The present invention solves this problem.

SUMMARY OF THE INVENTION

The present invention is directed to a catheter and particularly to a PTCA guiding catheter with a soft distal tip. The catheter comprises an elongated, tubular shaft having proximal and distal ends, a high tensile strength transition segment bonded to the distal end of the elongated tubular shaft, and a flexible, non-traumatic distal tip segment which is bonded to the distal end of the transition segment. The elongated tubular shaft may be of a multilayered design so that the requisite bending and torsional stiffnesses are achieved.

The applicant addresses the problem of low bond strength between the catheter shaft and soft distal tip created by catheters with wall thicknesses of less than 0.3 mm and a softer distal tip. To address this problem, the applicants employ a high tensile strength transition segment, selected from a group of thermoplastic elastomers having an ultimate tensile strength of at least 45 MPa. Further, the surface geometry of both the distal end of the elongated tubular shaft and the distal tip segment are modified to reduce stress concentration and increase surface area so that the adequate bonding to the distal tip segment is achieved. The use of a high tensile strength transition segment coupled with a modified surface geometry substantially increases the tensile strength of the bond between the catheter shaft and the distal soft tip.

In the preferred embodiment, the applicant creates a modified surface geometry on the distal end of the catheter shaft by removing two ungular sections on either side of the central longitudinal axis of the catheter shaft. Similarly, the surface geometry on the proximal end of the tip segment is modified by removing two ungular sections on either side of the central longitudinal axis of the tip segment. An alternative embodiment is the removal of more than two ungular sections on either or both of the distal end of the catheter shaft or the proximal end of the soft tip segment to further promote bonding.

In the preferred embodiment, a high tensile strength transition segment is bonded between the modified distal end of the catheter shaft and the modified proximal end of the soft tip segment using a technique such as injection molding. The transition segment is injected in a molten state to encapsulate the modified surface geometries of the distal catheter shaft and the proximal soft tip segment to create the improved lap joint. As a result, the improved lap joint achieves bond strengths between the catheter shaft and soft tip in excess of 18 N.

BRIEF DESCRIPTION OF THE DRAWINGS

FIG. 1 shows a plan view of the distal end of the catheter shaft showing the ungular sections which are removed from the distal portion of the shaft;

FIG. 6 is a plan view of the bonded assembly of the catheter shaft, the transition segment, and soft tip segment; and FIG. 7 is a cross-sectional view of the bonded assembly of the catheter shaft, the transition segment, and soft tip segment.

DETAILED DESCRIPTION OF THE PREFERRED EMBODIMENTS

Figure 2:
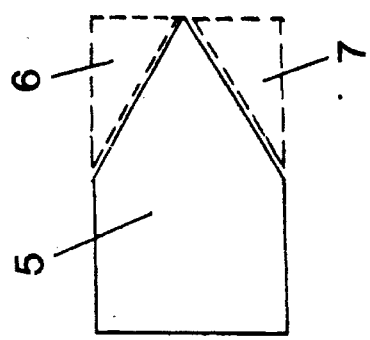
FIG. 2 shows a plan view of the soft tip segment showing the ungular sections which are removed from the proximal end of the soft tip segment.

Referring to FIG. 1, the surface geometry of the distal end of the catheter is modified by first inserting a polymer mandrel 1, sized to fit within the lumen of the catheter and of a material such as CELCON® acetyl which can be cut easily with a razor blade. A first ungular section 2 of the catheter shaft 3 is removed by orienting a razor blade at an angle of approximately 30° to the central longitudinal axis and plunge cutting through the catheter shaft and the mandrel. A second ungular section 4 of the catheter shaft 3 is removed by orienting and plunge cutting a razor blade 60° to the oblique plane formed by the first cut and 30° to the central longitudinal axis of the catheter shaft. The result of the removal of the ungular sections 2 and 4 is a distal end portion of the catheter shaft which is approximately 2.0 mm in length. Angles of less than 30°, for example 15°, create a longer distal end portion of the catheter shaft which increases the surface area for bonding and hence promotes stronger bonds with the soft tip segment. The polymer mandrel 1 is then removed from the lumen of the catheter shaft 3.

Referring to FIG. 2, the surface geometry of the proximal end of the soft tip segment 5 is modified by first inserting a polymer mandrel 1, sized to fit within the lumen of the catheter and of a material such as CELCON® acetyl which can be cut easily with a razor blade. The soft tip segment 5 is of a generally tubular shape with inner and outer diameters equal to those of the catheter shaft 3. The soft tip segment 5 is comprised of a blend of Shore 35D and 55D PEBAX® polyether-polyamide of overall length 0.1–15 mm and preferably 2.0 mm. A first ungular section 6 of the soft tip segment 5 is removed by orienting a razor blade at an angle of approximately 30° to the central longitudinal axis and plunge cutting through the soft tip segment and the mandrel. A second ungular section 7 of the soft tip segment 5 is removed by orienting and plunge cutting a razor blade 60° to the oblique plane formed by the first cut and 30° to the central longitudinal axis of the soft tip segment. Angles of less than 30°, for example 15°, create a longer modified proximal end of the soft tip segment which increases the surface area for bonding and hence promotes stronger bonds with the transition segment. The polymer mandrel 1 is then removed from the lumen of the soft tip segment 5.

Figure 3:
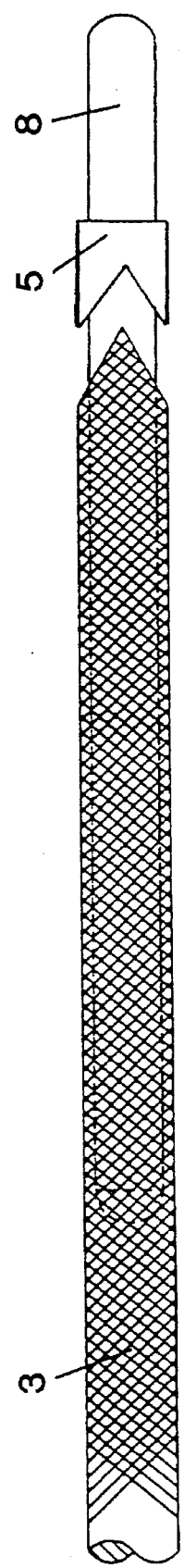
FIG. 3 is a plan view of the assembly of the distal end of the catheter shaft and the soft tip segment, showing both components with the ungular sections removed, and the stainless steel mandrel.

Referring to FIG. 3, the soft tip segment 5 and the catheter shaft 3 are assembled prior to bonding by first inserting a TEFLON® coated stainless steel mandrel 8 into the distal end of the catheter shaft to a depth of approximately 10 cm with approximately 5 cm extending distal to the end of the catheter shaft. The stainless steel mandrel 8, which is sized to a sliding fit with the lumen of the catheter shaft, provides rigidity and maintains concentricity for subsequent bonding of the catheter shaft 3 and the soft tip segment 5 assembly. The soft tip segment 5, is advanced over the distal end of the stainless steel mandrel 8 and placed with its modified proximal end 0.1–160 mm and preferably 0.5 mm from the modified distal end of the catheter shaft 3. The assembly is now prepared for the bonding operation.

Figure 4:
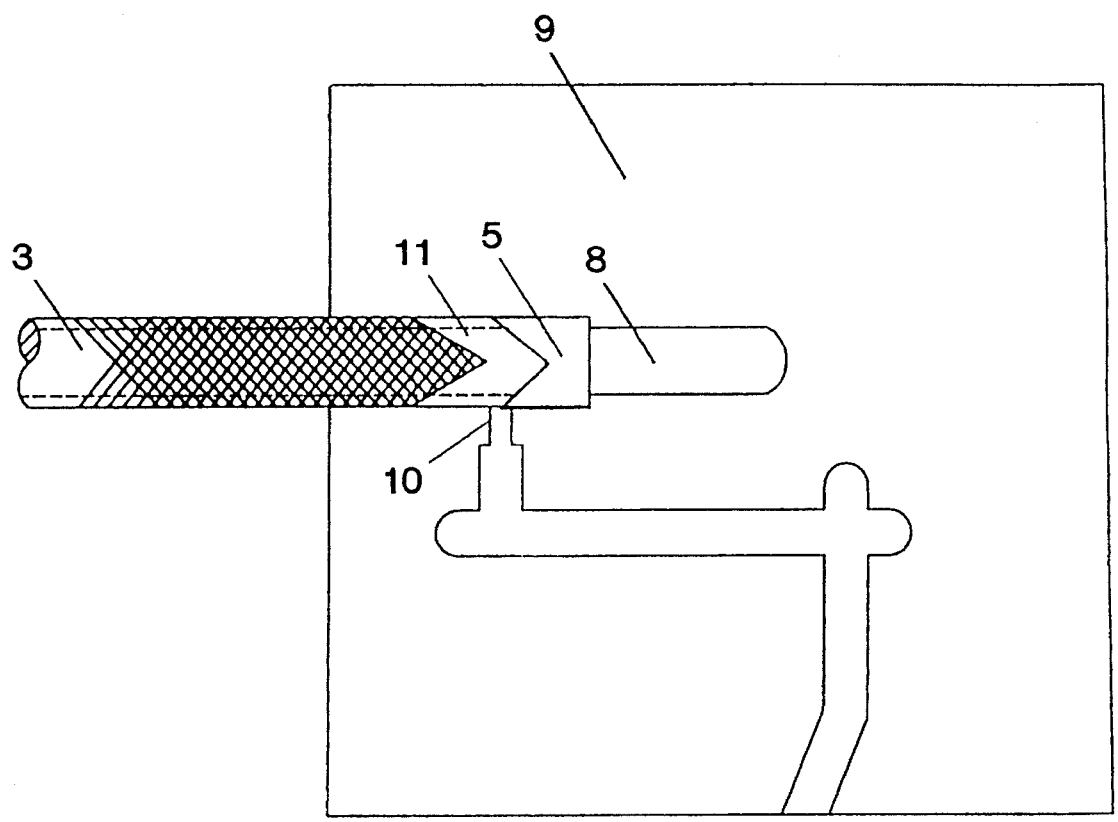
FIG. 4 shows a plan view of the injection mold cavity and the position of the assembly of FIG. 3 prior to injection molding.

Referring to FIG. 4, the assembly of FIG. 3 is then inserted into the mold cavity 9 of an injection mold machine such as an Arburg® 221-55-250. The 0.5 mm gap between the proximal end of the soft tip segment 5 and the distal end of the catheter shaft 3, modified as shown in FIG. 1, is centered over the mold gate 10. To promote bonding, the assembly of the stainless steel mandrel 8, the soft tip segment 5, and the catheter shaft 3 must be preheated to a temperature of approximately 130° C. for 90 seconds. A molten shot of Shore 55D PEBAX® polyether-polyamide material is injected at a nozzle temperature of approximately 265° C. and injection pressure of 500 psig and solidified to form a transition segment 11 between the catheter shaft 3 and soft tip segment 5. The transition segment 11 is of a generally tubular shape with inner and outer diameters equal to and coaxial with those of both the catheter shaft 3 and the soft tip segment 5. Alter injection molding, the bonded assembly of catheter shaft 3, stainless steel mandrel 8, transition segment 11, and soft tip segment 5 are removed from the mold cavity 9 and cooled to room temperature.

Figure 5:
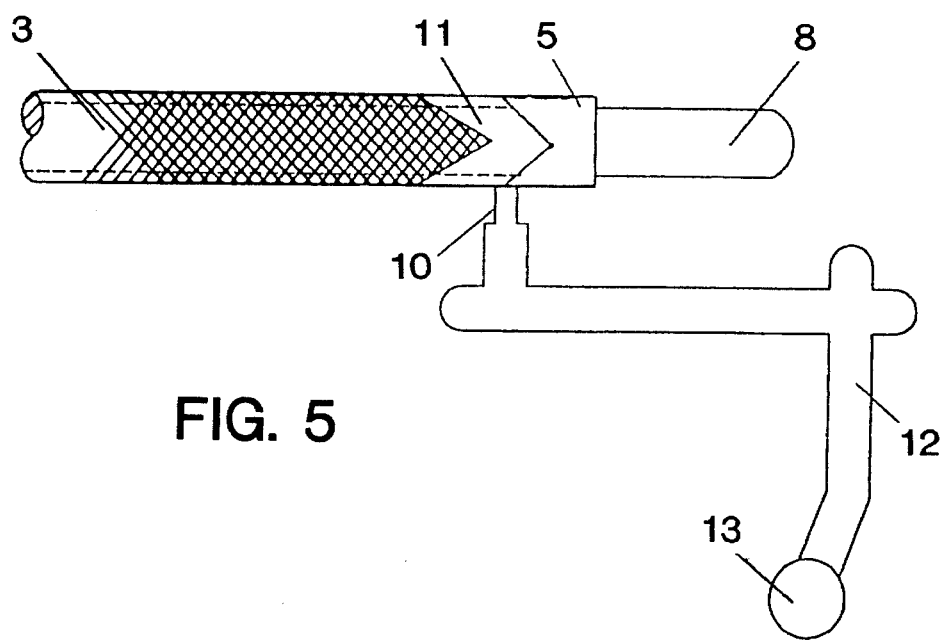
FIG. 5 shows a plan view of the assembly of FIG. 2 after injection molding showing the sprue and runner system which is removed in the subsequent trimming operation.

Referring to FIG. 5, the stainless steel mandrel 8 is removed from the lumen of the bonded assembly of catheter shaft 3, transition segment 11, and soft tip segment 5. The mold gate 10, runner system 12 and sprue assembly 13 is trimmed from the transition segment 11. The soft tip segment 5 is then cut to the desired overall length of approximately 2.0 mm.

Referring to FIG. 6, the catheter shaft 3, transition segment 11, and soft tip segment 5 are shown as a completed assembly. The result of the modified surface geometry of both the soft tip segment 5 and the distal end of the catheter shaft 3 is an increase in surface area and decreased stress concentration over the prior art. Modifying the distal end of the catheter shaft by removing the ungular sections (2 and 4 of FIG. 1) results in a surface area 200% that of a butt joint such as is disclosed by the '181 Wijayarathna patent, supra. Further, the surface area of the catheter shaft 3 is between 110–200% that of a frusto-conical joint such as that disclosed by the '292 Fletcher patent, supra. Also, stress concentration which is exhibited by the junctions of the flexible tubular elements of the '416 Macaulay patent, supra, is reduced on the catheter shaft 3 because the oblique planes which define the junction between the catheter shaft 3 and the transition segment 11 are not perpendicular to the tensile and flexural loads which are applied to the soft tip segment 5 during use.

Referring to FIG. 7, a cross-sectional view of the completed assembly of FIG. 6 is shown. The catheter shaft 3 is comprised of principally three layers as shown in FIG. 7: a lubricous liner 14, a composite layer 15 of wire braid and polymer, and an outer jacket polymer 16. The distal end of the catheter shaft 3 is shown bonded to the proximal end of the transition segment 11 and the distal end of the transition segment 11 is shown bonded to the proximal end of the soft tip segment 5.

The selection of materials for the transition segment 11 is based upon considerations of tensile strength, processing temperature compatibility with the polymers comprising the catheter shaft 3, and flexural modulus. A tensile strength in excess of 45 MPa is necessary to achieve a minimally acceptable bond strength of 18N between the catheter shaft 3 and the transition segment 11 when the wall thickness of the catheter shaft is less than 0.3 mm. This is because of the compromised bonding between the catheter shaft 3 and the transition segment 11 caused by the presence of the wire braid in the composite layer 15 and the lubricous liner 14. The transition segment 11 does not bond to the lubricous liner 14. The transition segment 11 does not bond to the composite layer 15 which is composed of wire and a polymer because of the wire. This is a consequence of the primary bonding mechanism being melt fusing. Since the wire cannot be melt fused to the transition segment 11, bonding between the transition segment 11 and the composite layer 15 is limited to the interstitial sites which are occupied by the polymer of the outer jacket 16. The transition segment 11 bonds well to the polymer of the outer jacket 16 because of melt compatibility. Because primary bonding occurs only at the interface of the transition segment 11, and because the polymer of the outer jacket 16 is only approximately one third of the overall catheter wall thickness, the transition segment 11 must be chosen for its tensile strength.

In order for the transition segment 11 to bond adequately to the outer jacket polymer 16, the transition segment 11 must have a processing temperature which is compatible with the outer jacket polymer 16. Further, the transition segment 11 must exhibit sufficient flexibility to facilitate the manipulation of the catheter shaft 3 through the patients vasculature. Sufficient flexibility is achieved where the flexural modulus of the transition segment 11 is less than 250 MPa. To meet the above requirements, the transition segment 11 is comprised of a Shore 55 D PEBAX® polyether-polyamide. This material has a compatible processing temperature to the outer jacket polymer 16, which is comprised of Shore 70D PEBAX® polyether-polyamide.

The selection of materials for the soft tip segment 5 is based upon considerations of flexural modulus and tensile strength. The flexural modulus is an indicator of the ability of the polymer to deflect adequately when the soft tip segment 5 contacts a wall of the patient's vasculature. The tensile strength must be sufficient to ensure an 18N minimum bond strength between the soft tip segment 5 and the transition segment 11. For a catheter wall thickness of less than 0.3 mm, a polymer exhibiting a minimum tensile strength of 30 MPa is required for the soft tip segment 5. These criteria are met with a material such as Shore 35 D PEBAX® polyether-polyamide or preferably a blend of 75% by weight 35 D PEBAX® and 25% 55 D PEBAX®.

It is noteworthy that the minimum tensile strength of the material comprising the soft tip segment 5 is significantly less than that required for the transition segment 11. This is because of the compromised bonding with the multi-layer catheter shaft 3 which requires a higher tensile strength material to compensate for the poor bonding which occurs between the transition segment 11 and both the composite layer 15 and the lubricous liner 14. Where the transition segment 11 is not comprised of multiple layers as is the catheter shaft 3, the soft tip segment 5 is bonded to the entire wall thickness of the transition segment 11. Thus, a lower tensile strength is allowable to achieve the minimum bond strength of 18 N.

To meet the criteria of requisite tensile strengths and flexural moduli, materials should be chosen for the transition segment 11 and soft tip segment 5 with a tensile strength ratio of greater than 1.25 and flexural modulus ratio of less than 15.0. The result of the material selections and the modified surface geometry of the catheter shaft and the soft tip segment 5 is a bonded assembly having a bond strength between the catheter shaft, transition segment 11, and soft tip segment in excess of 18N.

The preceding specific embodiments are illustrative of the practice of the invention. It is to be understood, however, that other expedients known to those skilled in the art or disclosed herein, may be employed without departing from the spirit of the invention or the scope of the appended claims.

| No. | Component |
|---|---|
| 1 | polymer mandrel |
| 2 | first ungular section of catheter shaft |
| 3 | catheter shaft |
| 4 | second ungular section of catheter shaft |
| 5 | soft tip segment |
| 6 | first ungular section of soft tip segment |
| 7 | second ungular section of soft tip segment |
| 8 | stainless steel mandrel |
| 9 | mold cavity |
| 10 | mold gate |
| 11 | transition segment |
| 12 | runner system |
| 13 | sprue assembly |
| 14 | catheter shaft lubricous liner |
| 15 | catheter shaft composite layer |
| 16 | catheter shaft outer jacket polymer |

What is claimed is:

1. A catheter comprising:

(a) an elongated soft tip segment having a proximal end and a distal end, the soft tip segment defining at least one lumen;

(b) an elongated transition segment having a proximal end and a distal end, the transition segment defining at least one lumen, the distal end of the transition segment having at least one ungular section, the proximal end of the transition segment having at least one ungular section;

(c) an elongated catheter shaft defining at least one lumen, the catheter shaft having a proximal end, a distal end, and a distal end portion, the distal end portion being shaped to mate with the proximal end of the transition segment, the distal end potion being bonded to the proximal end of the transition segment; and (d) the proximal end of the soft tip segment being shaped to mate with the distal end of the transition segment, the proximal end being bonded to the distal end of the transition segment.

2. A catheter according to claim 1 wherein the distal end portion of the catheter shaft is approximately 2.0 mm in length.

3. A catheter according to claim 1 wherein the elongated transition segment is approximately 0.5 mm in length.

4. A catheter according to claim 1 wherein the elongated transition segment is composed of a 55D Shore durometer polyether-polyamide material.

5. A catheter according to claim 1 wherein the elongated tip segment is approximately 2.0 mm in length.

6. A catheter according to claim 1 wherein the elongated soft tip segment is composed of a blend of Shore 35D and Shore 55D durometer polyether-polyamide material.

7. A catheter according to claim 1 wherein the elongated catheter shaft is at least partially composed of a 70D Shore durometer polyether-polyamide material.

8. A catheter according to claim 1 wherein the distal end of the transition segment has two ungular sections.

9. A catheter according to claim 8 wherein the two ungular sections have an angle of approximately 60 degrees therebetween.

10. A catheter according to claim 1 wherein the proximal end of the transition segment has two ungular sections.

11. A catheter according to claim 10 wherein the two ungular sections have an angle of approximately 60 degrees therebetween.

12. A catheter comprising:
   (a) a transition segment having a proximal end, a distal end, a central longitudinal axis, and defining at least one lumen, the proximal end having two ungular sections, the distal end having two ungular sections, one of each of the ungular sections being oriented at 30 degrees relative to the central longitudinal axis, the ungular sections of the proximal end having an angle of 60 degrees therebetween, the ungular sections of the distal end having an angle of 60 degrees therebetween;
   (b) a catheter shaft having a distal end portion and defining at least one lumen, the distal end portion being shaped to mate with the proximal end of the transition segment, the distal end portion being bonded to the proximal end of the transition segment; and
   (c) a soft tip segment having a proximal end and defining at least one lumen, the proximal end being shaped to mate with the distal end of the transition segment, the proximal end being bonded to the distal end of the transition segment.

13. The catheter according to claim 12 wherein the transition segment is comprised of a Shore 55D durometer polyether-polyamide material.

14. The catheter according to claim 12 wherein the soft tip segment is comprised of a blend of Shore 35D and Shore 55D durometer polyether-polyamide material.

15. The catheter according to claim 12 wherein the catheter shaft is at least partially comprised of a Shore 70D durometer polyether-polyamide material.

16. A catheter comprising:
   (a) a transition segment having a proximal end, a central longitudinal axis, and defining at least one lumen, the proximal end having two ungular sections, one of each of the ungular sections being oriented at 30 degrees relative to the central longitudinal axis, the ungular sections having an angle of 60 degrees therebetween; and
   (b) a catheter shaft having a distal end portion and defining at least one lumen, the distal end portion being shaped to mate with the proximal end of the transition segment, the distal end portion being bonded to the proximal end of the transition segment.

17. A catheter according to claim 16 wherein the transition segment is comprised of a Shore 55D durometer polyether-polyamide material.

18. A catheter according to claim 16 wherein the elongated catheter shaft is at least partially comprised of a 70D shore durometer polyether-polyamide material.

* * * * *